(12) United States Patent
Sato (10) Patent No.: US 6,908,610 B1
(45) Date of Patent: Jun. 21, 2005

(54) LONG-TERM STABILIZED FORMULATIONS

(75) Inventor: Yasushi Sato, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/914,641

(22) PCT Filed: Feb. 29, 2000

(86) PCT No.: PCT/JP00/01160

§ 371 (c)(1),
(2), (4) Date: Aug. 30, 2001

(87) PCT Pub. No.: WO00/51629

PCT Pub. Date: Sep. 8, 2000

(30) Foreign Application Priority Data

Mar. 1, 1999 (JP) .......................................... 11/052314

(51) Int. Cl.[7] .................. A61K 38/18; A61K 38/19
(52) U.S. Cl. ..................... 424/85.1; 530/351; 514/2
(58) Field of Search ................... 530/351; 424/85.1; 514/2

(56) References Cited

U.S. PATENT DOCUMENTS

| | | | |
|---|---|---|---|
| 4,915,945 A | 4/1990 | Pelzer et al. | |
| 4,992,419 A | 2/1991 | Woog et al. | |
| 5,358,708 A | 10/1994 | Patel | |
| 6,525,102 B1 * | 2/2003 | Chen et al. | 424/85.2 |

FOREIGN PATENT DOCUMENTS

| | | |
|---|---|---|
| EP | 853945 | 7/1998 |
| JP | 63-146829 | 6/1988 |
| JP | 3-287540 | 12/1991 |
| JP | 5-331071 | 12/1993 |
| WO | WO92/15614 | 9/1992 |
| WO | WO93 05799 | 4/1993 |
| WO | WO94/13143 | 6/1994 |
| WO | WO94/14465 | 7/1994 |

OTHER PUBLICATIONS

Nabuchi et al., 1998, Analytica Chimica Acta 365:301–307.*

Riisom, T., et al. "Effect of amino acids on the autoxidation of safflower oil in emulsions" J. AM. Oil Chem. Soc., 1980, vol. 57, No. 10, p. 354–359, Abstract; Table II, Figs. 1–6.

* cited by examiner

Primary Examiner—Elizabeth C. Kemmerer
(74) Attorney, Agent, or Firm—Morgan & Finnegan, LLP (57) ABSTRACT

A stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks and a content of Met-oxidized G-CSF of 1% or less after accelerated testing at 50° C. for 1 month or after accelerated testing at 60° C. for 2 weeks.

20 Claims, 3 Drawing Sheets

Before acceleration

After acceleration at 50°C for 1 month

FIG. 3

LONG-TERM STABILIZED FORMULATIONS

FIELD OF THE INVENTION

The present invention relates to G-CSF (granulocyte colony-stimulating factor) formulations, and particularly stabilized G-CSF formulations showing low active ingredient loss and low content of Met-oxidized G-CSF.

PRIOR ART

G-CSF is a glycoprotein having a molecular weight of about 20,000 and acting on precursor cells of neutrophils to promote their proliferation and differentiation to maturation.

Since we purified high-purity human G-CSF by culturing a cell line collected from tumor cells of a patient with cancer of the floor of the mouth, the human G-CSF gene was successfully cloned and, at present, recombinant human G-CSF can be produced in mass in microorganisms or animal cells by genetic engineering techniques. We also succeeded in converting this purified G-CSF into formulated products supplied to the market as antiinfective agents (Japanese Patent No. 2116515).

G-CSF is used in a very small amount, ie, a formulation containing 0.1–1000 μg (preferably 5–500 μg) of G-CSF is normally administered once to seven times per week per adult. However, this G-CSF is adsorptive to the walls of ampoules, syringes or the like. G-CSF is unstable and susceptible to extrinsic factors such as temperature, humidity, oxygen, UV rays or the like to undergo physical or chemical changes including association, polymerization or oxidation, resulting in substantial loss of activity.

Thus, various formulation designs were made to supply stable G-CSF formulations to the market. For example, formulations containing at least one member selected from the group consisting of (a) at least one amino acid selected from threonine, tryptophan, lysine, hydroxylysine, histidine, arginine, cysteine, cystine and methionine; (b) at least one sulfur-containing reducing agent; or (c) at least one antioxidant were proposed (Japanese Patent No. 2577744). G-CSF formulations containing a surfactant such as a Polysorbate as a stabilizer were also proposed (JPA No. 146826/88).

Lyophilized G-CSF formulations containing maltose, raffinose, sucrose, trehalose or an aminosugar were also reported, which are advantageous from the viewpoint of limiting deposits on the container to suppress chemical changes (JPA No. 504784/96).

Some products currently on the market contain a protein commonly used as a stabilizer such as human serum albumin or purified gelatin for suppressing such chemical or physical changes. However, addition of a protein as a stabilizer had problems such as the necessity of a very complicated process for removing contamination with viruses.

However, Met-oxidized G-CSF are more likely to be produced in the absence of such a protein, leading to the problem of deterioration.

DISCLOSURE OF THE INVENTION

An object of the present invention is to provide a G-CSF formulation, which is more stable even during long-term storage and which has a low content of Met-oxidized G-CSF.

As a result of careful studies to achieve the above object, we accomplished the present invention on the basis of the finding that a G-CSF formulation showing a high residual ratio of G-CSF and a low content of Met-oxidized G-CSF even after long-term storage can be obtained by adding a combination of specific amino acids as a stabilizer.

Accordingly, the present invention provides a stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks and a content of Met-oxidized G-CSF of 1% or less after accelerated testing at 50° C. for 1 month or after accelerated testing at 60° C. for 2 weeks.

The present invention also provides said G-CSF formulation containing one or more amino acids selected from the group consisting of lysine, histidine, arginine, aspartic acid, glutamic acid, threonine and asparagine; one or more amino acids selected from hydrophobic amino acids; and methionine.

The present invention also provides said G-CSF formulation wherein said hydrophobic amino acid is selected from phenylalanine, tryptophan and leucine.

The present invention also provides said G-CSF formulation containing one or more amino acids selected from the group consisting of lysine, histidine, arginine, aspartic acid and glutamic acid; one or more amino acids selected from the group consisting of phenylalanine, tryptophan and leucine; and methionine.

The present invention also provides said G-CSF formulation containing phenylalanine, arginine and methionine.

The present invention also provides said G-CSF formulation substantially free from protein as a stabilizer.

The present invention also provides said G-CSF formulation in the form of a lyophilized formulation.

The present invention also provides said G-CSF formulation further containing mannitol.

The present invention also provides said G-CSF formulation further containing a surfactant.

The present invention also provides said G-CSF formulation wherein said surfactant is a polyoxyethylene sorbitan alkyl ester.

The present invention also provides said G-CSF formulation wherein said surfactant is Polysorbate 20 and/or 80.

The present invention also provides said G-CSF formulation having a pH of 5–7.

The present invention also provides said G-CSF formulation having a pH of 5.5–6.8.

The present invention also provides said G-CSF formulation having a pH of 6.5.

The present invention also provides said G-CSF formulation wherein G-CSF is produced from CHO cells.

The present invention also provides a stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks, characterized in that it contains one or more amino acids selected from the group consisting of lysine, histidine, arginine, aspartic acid, glutamic acid, threonine and asparagine; and one or more amino acids selected from hydrophobic amino acids; and it has a pH of 5–7.

The present invention also provides a stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks, characterized in that it contains one or more amino acids selected from the group consisting of lysine, histidine, arginine, aspartic acid and glutamic acid; and one or more amino acids selected from the group consisting of phenylalanine, tryptophan and leucine; and it has a pH of 5–7.

The present invention also provides either one of said G-CSF formulations having a pH of 6.5.

The present invention also provides a method for inhibiting a physiologically active protein containing a methionine residue from producing a variant oxidized at the methionine residue, comprising adding methionine to a composition containing said protein.

The present invention also provides said method wherein said physiologically active protein is a cytokine or a physiologically active peptide.

The present invention also provides said method wherein said physiologically active protein is a colony-stimulating factor or PTH.

The present invention also provides said method wherein said physiologically active protein is G-CSF, erythropoietin or PTH.

The present invention also provides said method wherein other proteins are not present as stabilizers.

The present invention also provides said method wherein said composition containing a physiologically active protein having a methionine residue is lyophilized or in the form of a solution.

The present invention also provides a stabilized composition containing a physiologically active protein having a methionine residue, further containing methionine and one or more other amino acids.

The present invention also provides said stabilized composition containing a physiologically active protein having a methionine residue wherein said amino acid is one or more selected from the group of consisting of lysine, histidine, arginine, aspartic acid, glutamic acid, phenylalanine, tryptophan, leucine, isoleucine, valine, alanine, proline, glycine, serine, threonine, asparagine, glutamine and tyrosine.

The present invention also provides said stabilized composition containing a physiologically active protein having a methionine residue, characterized in that it is free from other proteins as stabilizers.

BRIEF DESCRIPTION OF THE DRAWINGS

In FIG. 3, the highest peaks at the center correspond to intact PTH, and peaks designated as Met-8 and Met-18 correspond to PTH oxidized at the 8th methionine residue and the 18th methionine residue, respectively.

THE MOST PREFERRED EMBODIMENTS OF THE INVENTION

G-CSF used for formulations of the present invention includes any high-purity human G-CSF. Specifically, it may be derived from natural sources or obtained by genetic recombination so far as it has substantially the same biological activity as that of mammalian, particularly human G-CSF. Genetically recombinant G-CSF may have the same amino acid sequence as that of natural G-CSF or may contain deletion, substitution or addition of one or more amino acids in said amino acid sequence so far as it has said biological activity. G-CSF in the present invention may be prepared by any process, eg, it may be extracted and purified by various techniques from cultures of a human tumor cell line or may be produced by genetic engineering in cells of *E. coli*, yeast, Chinese hamster ovary (CHO), C127 or the like and then extracted and purified by various techniques. Preferably. G-CSF is produced in *E. coli*, yeast or CHO cells by genetic recombination. Most preferably, G-CSF is produced in CHO cells by genetic recombination.

Preferably, G-CSF formulations of the present invention are substantially free from protein such as human serum albumin or purified gelatin as a stabilizer.

G-CSF formulations of the present invention are very stable as compared with previously known G-CSF formulations as they have a residual ratio of G-CSF of 90% or more, preferably 95% or more after long-term storage testing at 25° C. for 3 months, or a residual ratio of G-CSF of 90% or more, preferably 95% or more after long-term storage testing at 40° C. for 2 months, or a residual ratio of G-CSF of 90% or more, preferably 95% or more after accelerated testing at 50° C. for 1 month, or a residual ratio of G-CSF of 90% or more, preferably 95% or more after accelerated testing at 60° C. for 2 weeks and a content of Met-oxidized G-CSF of 1% or less, preferably below detection limit after accelerated testing at 50° C. for 1 month or after accelerated testing at 60° C. for 2 weeks.

An example of G-CSF formulations of the present invention is a G-CSF formulation containing one or more amino acids selected from the group consisting of lysine, histidine, arginine, aspartic acid, glutamic acid, threonine and asparagine, preferably one or more amino acids selected from the group consisting of lysine, histidine, arginine, aspartic acid and glutamic acid; one or more amino acids selected from hydrophobic amino acids, preferably one or more amino acids selected from the group consisting of phenylalanine, tryptophan and leucine; and methionine.

Another example of G-CSF formulations of the present invention is a stable G-CSF formulation having a residual ratio of G-CSF of 90% or more after long-term storage testing at 25° C. for 3 months or a residual ratio of G-CSF of 96% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks and a content of Met-oxidized G-CSF of 1% or less after accelerated testing at 50° C. for 1 month or after accelerated testing at 60° C. for 2 weeks, characterized in that it contains one or more amino acids selected from the group consisting of lysine, histidine, arginine, aspartic acid, glutamic acid, threonine and asparagine, preferably one or more amino acids selected from the group consisting of lysine, histidine, arginine, aspartic acid and glutamic acid; one or more amino acids selected from hydrophobic amino acids, preferably one or more amino acids selected from the group consisting of phenylalanine, tryptophan and leucine; and methionine; and it has a pH of 5–7.

Amino acids used in the present invention include free amino acids and salts thereof such as sodium salts, potassium salts and hydrochlorides. Formulations of the present invention may contain D-, L- and DL-variants of these amino acids, more preferably L-variants and salts thereof.

The amount of amino acids to be added to formulations of the present invention can be determined in a preferred range using the test method described later depending on the type of the amino acid used. Generally, a final dose of 0.001–50 mg/ml is added. For example, phenylalanine is preferably added at 0.1–25 mg/ml, more preferably 1–20 mg/ml, arginine is preferably added at 0.1–25 mg/ml, more preferably 1–20 mg/ml, and methionine is preferably added at 0.001–5 mg/ml, more preferably 0.01–4 mg/ml.

Formulations of the present invention may contain isotonizing agents, eg, polyethylene glycol; and sugars such as dextran, mannitol, sorbitol, inositol, glucose, fructose, lactose, xylose, mannose, maltose, sucrose and raffinose. Mannitol is especially preferred. The amount of mannitol added into formulations is 1–100 mg/ml, more preferably 5–60 mg/ml.

Formulations of the present invention may further contain surfactants. Typical examples of surfactants include:

nonionic surfactants, eg, sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6–18;

anionic surfactants, eg, alkyl sulfates having a C10–18 alkyl group such as sodium cetylsulfate, sodium laurylsulfate, sodium oleylsulfate; polyoxyethylene alkyl ether sulfates having an average EO mole number of 2–4 and a C10–18 alkyl group such as sodium polyoxyethylene laurylsulfate; alkyl sulfosuccinic acid ester salts having a C8–18 alkyl group such as sodium laurylsulfosuccinate; and natural surfactants, eg, lecithin; glycerophospholipids; sphingophospholipids such as sphingomyelin; sucrose fatty acid esters of C12–18 fatty acids. One or more of these surfactants may be added in combination to formulations of the present invention.

Preferred surfactants are polyoxyethylene sorbitan fatty acid esters, more preferably Polysorbates 20, 21, 40, 60, 65, 80, 81, 85, most preferably Polysorbates 20 and 80.

The amount of surfactants to be added to G-CSF-containing formulations of the present invention is typically 0.0001–1 parts by weight per part by weight of G-CSF, preferably 0.01–5 parts by weight per part by weight of G-CSF, and most preferably 0.2–2 parts by weight per part by weight of G-CSF.

Preferably, G-CSF formulations of the present invention have a pH of 5–7, more preferably 5.5–6.8, still more preferably 6–6.7, and most preferably 6.5.

G-CSF formulations of the present invention may further contain diluents, solubilizing agents, excipients, pH-modifiers, soothing agents, buffers, sulfur-containing reducing agents, antioxidants or the like, if desired. For example, sulfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added may also be contained, eg, inorganic salts such as sodium chloride, potassium chloride, calcium chloride, sodium phosphate, potassium phosphate, sodium bicarbonate; and organic salts such as sodium citrate, potassium citrate, sodium acetate.

G-CSF formulations of the present invention include solution formulations, lyophilized formulations, spray-dried formulations, etc. Lyophilized formulations are most preferred.

Formulations of the present invention can be prepared by dissolving these components in an aqueous buffer known in the art of solution formulations such as phosphate buffers (preferably sodium monohydrogen phosphate—sodium dihydrogen phosphate system) and/or citrate buffers (preferably sodium citrate buffer) to prepare a solution formulation, or lyophilizing or spray-drying thus prepared solution formulation by standard procedures.

Stabilized G-CSF-containing formulations of the present invention are normally administered via parenteral routes such as injection (subcutaneous, intravenous or intramuscular injection) or percutaneous, mucosal, nasal or pulmonary administration, but may also be orally administered.

G-CSF formulations of the present invention are normally packed in a sealed and sterilized plastic or glass container, and dissolved in pure water (sterilized water for injection) before use.

The amount of G-CSF contained in formulations of the present invention can be determined depending on the type of the disease to be treated, the severity of the disease, the age of the patient or other factors, but generally ranges from 1 to 1000 μg/mL, preferably 10 to 800 μg/mL, more preferably 50 to 500 μg/mL.

Formulations of the present invention are clinically very useful as they were found to improve protective functions based on immune response such as resistance of the patient or activity when they were coadministered with drugs such as antibiotics, antibacterial agents or anticancer agents in the chemotherapy of infectious diseases or cancer. Therefore, formulations of the present invention can be administered in combination with these drugs.

As demonstrated in the examples below, G-CSF formulations of the present invention show a very good residual ratio of G-CSF after long-term storage testing at 25° C. for 3 months or long-term storage testing at 40° C. for 2 months or accelerated testing at 50° C. for 1 month or accelerated testing at 60° C. for 2 weeks. Moreover, a small content of Met-oxidized G-CSF was observed after accelerated testing at 50° C. for 1 month or accelerated testing at 60° C. for 2 weeks. G-CSF formulations of the present invention have a residual ratio of C—CSF of 90% or more, preferably 95% or more after long-term storage testing at 25° C. for 3 months, or a residual ratio of G-CSF of 90% or more, preferably 95% or more after long-term storage testing at 40° C. for 2 months, or a residual ratio of G-CSF of 90% or more, preferably 95% or more after accelerated testing at 50° C. for 1 month, or a residual ratio of G-CSF of 90% or more, preferably 95% or more after accelerated testing at 60° C. for 2 weeks and a content of Met-oxidized G-CSF of 1% or less, preferably below detection limit after accelerated testing at 50° C. for 1 month or after accelerated testing at 60° C. for 2 weeks.

It was observed from the results of the examples below that the residual ratio of G-CSF in formulations of the present invention after long-term storage at normal temperatures can be improved by adding one or more amino acids selected from the group consisting of lysine, histidine, arginine, aspartic acid, glutamic acid, threonine and asparagine and one or more amino acids selected from hydrophobic amino acids and that the content of Met-oxidized G-CSF can be kept below detection limit by adding methionine. Without wishing to be bound to any specific theory, we assumed that the added methionine is oxidized in place of methionine residues of G-CSF so that the content of Met-oxidized G-CSF decreases.

When methionine is added to a compositions of a physiologically active protein having a methionine residue, which is more susceptible to production of a variant oxidized at the methionine residue and has a physiological activity in a small amount, said physiologically active protein can also be prevented from producing a variant oxidized at the methionine residue according to the present invention. Addition of methionine seems to be especially effective when said physiologically active protein composition is free from other proteins as stabilizers or when said protein composition is lyophilized or in the form of a solution because the variant of said protein oxidized at the methionine residue is more likely to be produced in such cases.

When other one or more amino acids are added to a composition of the present invention, a stabilized composition containing a physiologically active protein having a methionine residue can also be prepared, which is inhibited from producing a variant oxidized at the methionine residue as well as inhibited from decomposition, aggregation or the like of said physiologically active protein.

Amino acids that can be added for this purpose include lysine, histidine, arginine, aspartic acid, glutamic acid, phenylalanine, tryptophan, leucine, isoleucine, valine, alanine, proline, glycine, serine, threonine, asparagine, glutamine and tyrosine, preferably histidine, arginine and phenylalanine.

Physiologically active proteins of the present invention include, for example:

cytokines such as interleukins (eg, IL-1 to IL-13), colony-stimulating factors (eg, granulocyte colony-stimulating factor (G-CSF), macrophage colony-stimulating factor (M-CSF), granulocyte/macrophage colony-stimulating factor (GM-CSF), erythropoietin (EPO)), interferons (eg, IFN-α, β, γ), tumor necrosis factors (eg, TNF-α, TNF-β), transforming growth factor (TGF), platelet-derived growth factor (PDGF), LIF (leukemia inhibitory factor), oncostatin M (OSM), migration inhibitory factor (MIF), chemokines (eg, IL-8. LD78, MCP-1);

physiologically active peptides such as insulin, glucagon, parathyroid hormone (PTH), gastrin, selectin, cholecystokinin, gastric inhibitory polypeptides, substance P, motilin, spleen polypeptides, neurotensin, enteroglucagon, gastrin-releasing peptides, somatostatin-28, dynorphin, galanin, vanilone, pancreostatin and zeopsin;

bioenzymes such as enzymes having a methionine residue at the active center (eg, malate dehydrogenase);

or variants thereof.

Physiologically active proteins of the present invention are preferably cytokines or physiologically active peptides, more preferably colony-stimulating factors such as G-CSF or erythropoietin or PTH, still more preferably G-CSF, erythropoietin or PTH.

The following examples further illustrate the present invention, without limiting the same thereto. Various changes and modifications can be made by those skilled in the art on the basis of the description of the invention, and such changes and modifications are also included in the present invention.

EXAMPLES

Test Method

Formulated solutions containing various components in the amounts shown in Tables 1 and 2 below were prepared and aseptic-filtered, and then precisely 1 mL each was aseptically packed in a vial and lyophilized. After completion of lyophilization, the vial was completely capped to prepare G-CSF lyophilized formulations.

TABLE 1

|  | G-CSF | Phenylalanine | Arginine | Methionine | Mannitol | Polysorbate 20 | pH buffer |
| --- | --- | --- | --- | --- | --- | --- | --- |
| Sample 1 | 250 μg | 10 mg | 10 mg | 0 | 50 mg | 0.1 mg | Phosphate, pH 7.4 |
| Sample 2 | 250 μg | 10 mg | 10 mg | 0 | 50 mg | 0.1 mg | Phosphate, pH 6.5 |
| Sample 3 | 100 μg | 0 mg | 0 mg | 0 | 50 mg | 0.1 mg | Phosphate, pH 6.5 |
| Sample 4 | 100 μg | 10 mg | 0 mg | 0 | 50 mg | 0.1 mg | Phosphate, pH 6.5 |
| Sample 5 | 100 μg | 0 mg | 10 mg | 0 | 50 mg | 0.1 mg | Phosphate, pH 6.5 |

TABLE 1-continued

| | G-CSF | Amino acid 1 | Amino acid 2 | Methionine | Mannitol | Polysorbate 20 | pH buffer |
|---|---|---|---|---|---|---|---|
| Sample 6 | 100 μg | 10 mg | 10 mg | 0 | 50 mg | 0.1 mg | Phosphate, pH 6.5 |
| Sample 7 | 250 μg | 0 mg | 0 mg | 0 | 50 mg | 0.1 mg | Phosphate, pH 6.5 |
| Sample 8 | 250 μg | 10 mg | 0 mg | 0 | 50 mg | 0.1 mg | Phosphate, pH 6.5 |
| Sample 9 | 250 μg | 0 mg | 10 mg | 0 | 50 mg | 0.1 mg | Phosphate, pH 6.5 |
| Sample 10 | 250 μg | 10 mg | 10 mg | 0 | 50 mg | 0.1 mg | Phosphate, pH 6.5 |

| | G-CSF | Amino acid 1 | Amino acid 2 | Methionine | Mannitol | Polysorbate 20 | pH buffer |
|---|---|---|---|---|---|---|---|
| Sample 11 | 100 μg | Phenylalanine | Lysine | 0 | 50 mg | 0.1 mg | Phosphate, pH 6.5 |
| Sample 12 | 100 μg | Phenylalanine | Histidine | 0 | 50 mg | 0.1 mg | Phosphate, pH 6.5 |
| Sample 13 | 100 μg | Phenylalanine | Arginine | 0 | 50 mg | 0.1 mg | Phosphate, pH 6.5 |
| Sample 14 | 100 μg | Phenylalanine | Aspartic acid | 0 | 50 mg | 0.1 mg | Phosphate, pH 6.5 |
| Sample 15 | 100 μg | Phenylalanine | Glutamic acid | 0 | 50 mg | 0.1 mg | Phosphate, pH 6.5 |
| Sample 16 | 100 μg | Phenylalanine | Serine | 0 | 50 mg | 0.1 mg | Phosphate, pH 6.5 |
| Sample 17 | 100 μg | Phenylalanine | Threonine | 0 | 50 mg | 0.1 mg | Phosphate, pH 6.5 |
| Sample 18 | 100 μg | Phenylalanine | Tyrosine | 0 | 50 mg | 0.1 mg | Phosphate, pH 6.5 |
| Sample 19 | 100 μg | Phenylalanine | Asparagine | 0 | 50 mg | 0.1 mg | Phosphate, pH 6.5 |
| Sample 20 | 100 μg | Phenylalanine | Glutamine | 0 | 50 mg | 0.1 mg | Phosphate, pH 6.5 |

In each case, 10 mg phenylalanine was added (equivalent to 60 mM). Amino acid 2 was added in an amount equivalent to 60 mM (equimolar to amino acid 1).

| | G-CSF | Amino acid 1 | Amino acid 2 | Methionine | Mannitol | Polysorbate 20 | pH buffer |
|---|---|---|---|---|---|---|---|
| Sample 21 | 100 μg | Arginine | Alanine | 0 | 50 mg | 0.1 mg | Phosphate, pH 6.5 |
| Sample 22 | 100 μg | Arginine | Valine | 0 | 50 mg | 0.1 mg | Phosphate, pH 6.5 |
| Sample 23 | 100 μg | Arginine | Leucine | 0 | 50 mg | 0.1 mg | Phosphate, pH 6.5 |
| Sample 24 | 100 μg | Arginine | Isoleucine | 0 | 50 mg | 0.1 mg | Phosphate, pH 6.5 |
| Sample 25 | 100 μg | Arginine | Methionine | 0 | 50 mg | 0.1 mg | Phosphate, pH 6.5 |
| Sample 26 | 100 μg | Arginine | Tryptophan | 0 | 50 mg | 0.1 mg | Phosphate, pH 6.5 |
| Sample 27 | 100 μg | Arginine | Phenylalanine | 0 | 50 mg | 0.1 mg | Phosphate, pH 6.5 |
| Sample 28 | 100 μg | Arginine | Proline | 0 | 50 mg | 0.1 mg | Phosphate, pH 6.5 |
| Sample 29 | 100 μg | Arginine | Glycine | 0 | 50 mg | 0.1 mg | Phosphate, pH 6.5 |
| Sample 30 | 100 μg | Arginine | Serine | 0 | 50 mg | 0.1 mg | Phosphate, pH 6.5 |
| Sample 31 | 100 μg | Arginine | Threonine | 0 | 50 mg | 0.1 mg | Phosphate, pH 6.5 |
| Sample 32 | 100 μg | Arginine | Asparagine | 0 | 50 mg | 0.1 mg | Phosphate, pH 6.5 |
| Sample 33 | 100 μg | Arginine | Glutamine | 0 | 50 mg | 0.1 mg | Phosphate, pH 6.5 |

In each case, 10 mg arginine was added (equivalent to 60 mM). Amino acid 2 was added in an amount equivalent to 60 mM (equimolar to amino acid 1).

TABLE 2

| | G-CSF | Phe | Arg | Met | Mannitol | Polysorbate 20 | pH buffer |
|---|---|---|---|---|---|---|---|
| Sample 34 | 100 μg | 10 mg | 10 mg | 0 mg | 25 mg | 0.1 mg | Phosphate, pH 6.5 |
| Sample 35 | 100 μg | 10 mg | 10 mg | 0.1 mg | 25 mg | 0.1 mg | Phosphate, pH 6.5 |
| Sample 36 | 100 μg | 10 mg | 10 mg | 1 mg | 25 mg | 0.1 mg | Phosphate, pH 6.5 |

Thus aseptically prepared G-CSF-containing lyophilized formulations were allowed to stand in an incubator at 60° C. for 2 weeks and 1 month; at 50° C. for 1, 2 and 3 months; at 40° C. for 2, 4 and 6 months; and at 25° C. for 3 and 6 months.

Accelerated and unaccelerated formulations were dissolved in precisely 1 mL of pure water to prepare test samples for the assays described below.

The residual ratio of G-CSF (% residual) in each vial was determined by method 1 below. The content of Met-oxidized G-CSF in each vial was also determined by method 2 below.

Method 1

The content of G-CSF in each sample was assayed by reverse phase high-speed liquid chromatography using a C4 reverse phase column (4.6 mm×250 mm, 300 angstroms) with a mobile phase consisting of pure water, acetonitrile and trifluoroacetic acid. The amount equivalent to 5 μg of G-CSF was injected and G-CSF was eluted with an acetonitrile gradient and spectroscopically detected at a wavelength of 215 nm.

The G-CSF content determined by this method was used to calculate the percentage (%) of residual G-CSF according to the following equation after acceleration at 60° C. for 2 weeks and 50° C. for 1 month and after storage at 60° C. for 2 weeks and 1 month; 50° C. for 1, 2 and 3 months; 40° C. for 2, 4 and 6 months; and 25° C. for 3 and 6 months.

$$\text{Residual ratio (\%)} = \frac{(G\text{-}CSF \text{ content after acceleration for a test period})}{(G\text{-}CSF \text{ content before acceleration})} \times 100$$

Method 2

Intact G-CSF and Met-oxidized G-CSF in each sample were assayed by reverse phase high-speed liquid chromatography using a C4 reverse phase column (4.6 mm×250 mm, 300 angstroms) with a mobile phase consisting of pure water, acetonitrile and trifluoroacetic acid. G-CSF was eluted with an acetonitrile gradient and spectroscopically detected at a wavelength of 215 nm.

The peak areas of intact G-CSF and Met-oxidized G-CSF determined by this method were used to calculate the content of Met-oxidized G-CSF according to the following equation after acceleration at 60° C. for 2 weeks and 50° C. for 1 month.

$$\text{Content of Met-oxidized } G\text{-}CSF\ (\%) = \frac{(\text{Met-oxidized } G\text{-}CSF)}{(\text{intact } G\text{-}CSF) + (\text{Met-oxidized } G\text{-}CSF)} \times 100$$

Example 1

Effect of Varying pHs on the Residual Ratio of G-CSF

The residual ratio of G-CSF in samples 1 and 2 prepared at different pHs shown in Table 1 were calculated according to the equation shown in method 1 after accelerated testing at 60° C. for 2 weeks and 50° C. for 1 month. The results are shown in Table 3.

TABLE 3

|  | Sample 1, pH 7.4 | Sample 2, pH 6.5 |
|---|---|---|
| 50° C., 1 month | 97.7 | 99.7 |
| 60° C., 2 weeks | 95.8 | 97.1 |

Comparable or more stability was observed with the formulation at pH 6.5 as compared with pH 7.4.

Example 2

Effect of Various Amino Acids on the Residual Ratio of G-CSF (1)

The residual ratio of G-CSF in samples 3–6 (G-CSF content 100 μg) and samples 7–10 (G-CSF content 250 μg) prepared with various amino acids shown in Table 1 were calculated according to the equation shown in method 1 after accelerated testing at 60° C. for 2 weeks and 50° C. for 1 month. The results are shown in Tables 4 and 5.

TABLE 4

| Formulations containing 100 μg G-CSF | | | | |
|---|---|---|---|---|
|  | Sample 3 | Sample 4 | Sample 5 | Sample 6 |
| Phenylalanine | No | 10 mg | No | 10 mg |
| Arginine | No | No | 10 mg | 10 mg |
| 50° C., 1 month | 72.9% | 84.8% | 82.4% | 98.3% |
| 60° C., 2 weeks | 67.2% | 77.9% | 68.8% | 95.0% |

TABLE 5

| Formulations containing 250 μg G-CSF | | | | |
|---|---|---|---|---|
|  | Sample 7 | Sample 8 | Sample 9 | Sample 10 |
| Phenylalanine | No | 10 mg | No | 10 mg |
| Arginine | No | No | 10 mg | 10 mg |
| 50° C., 1 month | 76.6% | 88.1% | 96.3% | 99.7% |
| 60° C., 2 weeks | 74.0% | 78.1% | 90.7% | 97.1% |

At any G-CSF content, stability is improved in formulations added with phenylalanine alone or arginine alone as compared with formulations containing no amino acid, but to an insufficient extent. Marked improvement in stability was observed by combining phenylalanine with arginine.

Example 3

Effect of Various Amino Acids on the Residual Ratio of G-CSF (2)

The residual ratio of remaining G-CSF in samples 11–20 (containing phenylalanine as amino acid 1 and any of lysine, histidine, arginine, aspartic acid, glutamic acid, serine, threonine, tyrosine, asparagine and glutamine as amino acid 2) and samples 21–33 (containing arginine as amino acid 1 and any of alanine, valine, leucine, isoleucine, methionine, tryptophan, phenylalanine, proline, glycine, serine, threonine, asparagine and glutamine as amino acid 2) prepared with various amino acids shown in Table 1 were calculated according to the equation shown in method 1 after accelerated testing at 60° C. for 2 weeks and 50° C. for 1 month. The results are shown in Tables 6 and 7.

TABLE 6

|  | 50° C., 1 month | 60° C., 2 weeks |
|---|---|---|
| Sample 11 | 92.8% | 91.2% |
| Sample 12 | 98.8% | 97.5% |
| Sample 13 | 98.0% | 96.0% |
| Sample 14 | 95.7% | 96.7% |
| Sample 15 | 95.6% | 94.0% |
| Sample 16 | 88.4% | 87.8% |
| Sample 17 | 96.4% | 90.7% |
| Sample 18 | 84.6% | 81.7% |
| Sample 19 | 95.0% | 95.3% |
| Sample 20 | 89.8% | 87.2% |

TABLE 7

|  | 50° C., 1 month | 60° C., 2 weeks |
|---|---|---|
| Sample 21 | 89.0% | 84.4% |
| Sample 22 | 88.9% | 86.5% |
| Sample 23 | 96.3% | 96.2% |
| Sample 24 | 88.5% | 89.3% |
| Sample 25 | 95.5% | 88.5% |
| Sample 26 | 101.4% | 98.6% |
| Sample 27 | 97.0% | 95.7% |
| Sample 28 | 89.4% | 82.5% |
| Sample 29 | 90.9% | 71.2% |
| Sample 30 | 89.2% | 85.2% |
| Sample 31 | 90.6% | 87.3% |
| Sample 32 | 94.0% | 88.6% |
| Sample 33 | 90.1% | 84.6% |

Marked improvement in long-term storage stability was observed by combining phenylalanine with lysine, phenylalanine with histidine, phenylalanine with arginine, phenylalanine with aspartic acid, phenylalanine with glutamic acid, phenylalanine with threonine, or phenylalanine with asparagine, or combining arginine with leucine, arginine with tryptophan, or arginine with phenylalanine.

Example 4

Long-Term Storage Testing

The residual ratio of G-CSF in samples containing 100 μg or 250 μg G-CSF and 10 mg phenylalanine, 10 mg arginine and 1 mg methionine were calculated according to the equation shown in method 1 after storage at 60° C. for 2 weeks and 1 month; 50° C. for 1, 2 and 3 months; 40° C. for 2, 4 and 6 months; and 25° C. for 3 and 6 months. The results are shown in Table 8.

TABLE 8

| G-CSF | 60° C. | | 50° C. | | | 40° C. | | | 25° C. | |
|---|---|---|---|---|---|---|---|---|---|---|
| (μg) | 2W[1] | 1M[2] | 1M | 2M | 3M | 2M | 4M | 6M | 3M | 6M |
| 100 | 98.3 | 96.2 | 99.9 | 100.1 | 95.9 | 101.0 | 100.0 | 98.8 | 97.0 | 98.0 |
| 250 | 97.2 | 94.5 | 98.7 | 98.0 | 96.7 | 99.4 | 99.3 | 98.1 | 98.5 | 100.6 |

[1]week
[2]month

Both formulations showed excellent residual ratio of G-CSF.

Example 5

Effect of Addition of Amino Acids on the Content of Met-Oxidized G-CSF

Figure 1:
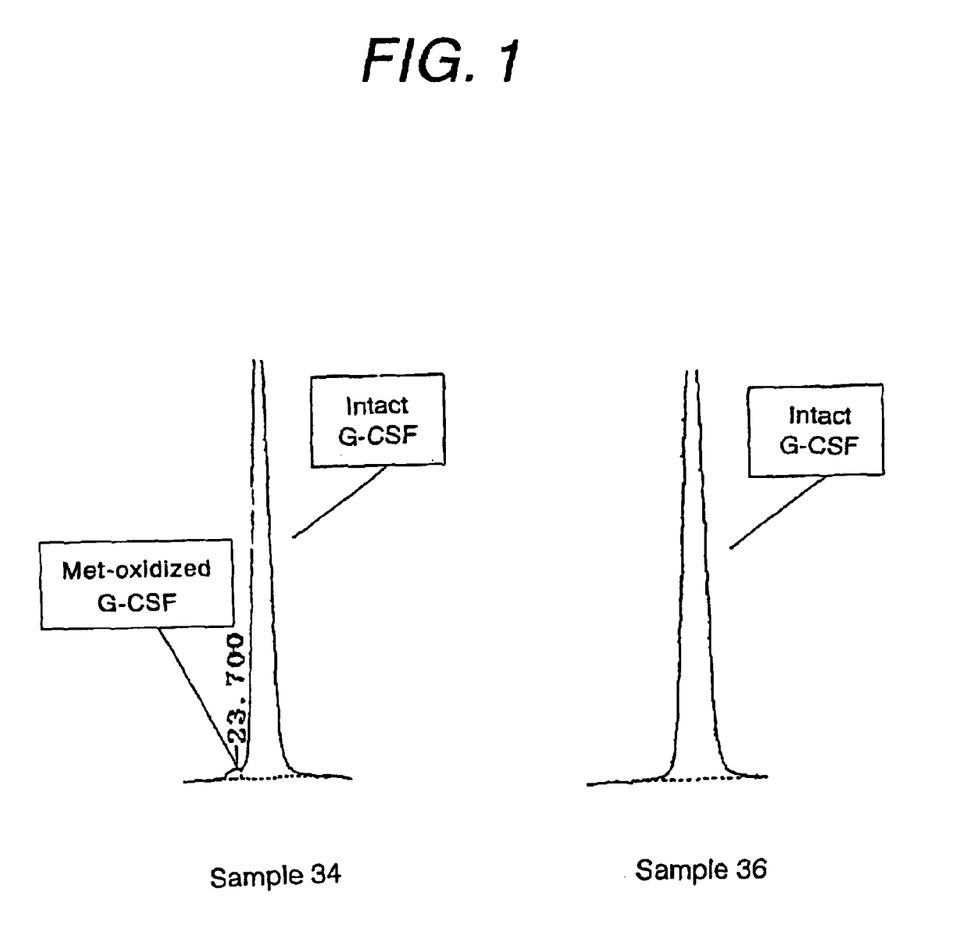
FIG. 1 shows chromatograms of samples 34 and 36 as assayed by method 2 described later after accelerated testing at 60° C. for 2 weeks.
Figure 2:
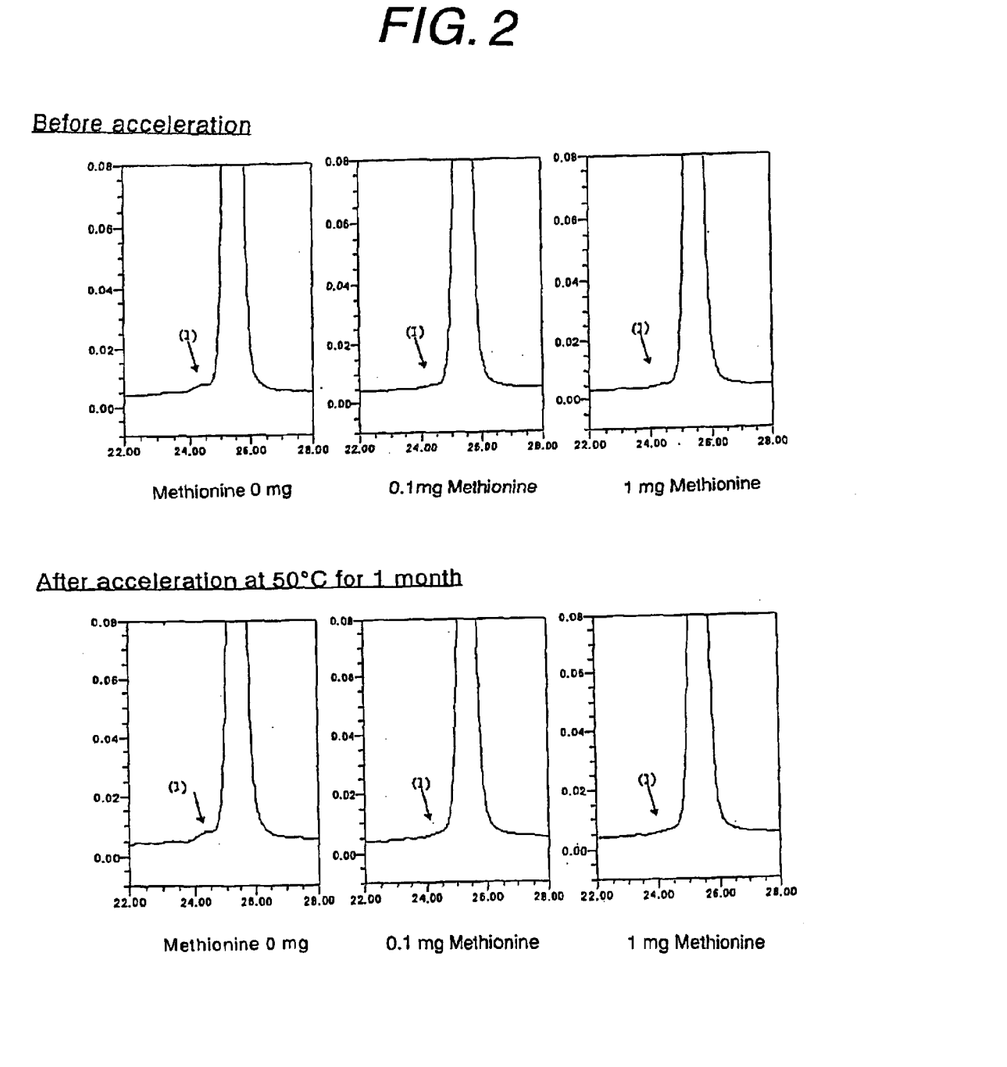
FIG. 2 shows chromatograms of samples 34–36 as assayed by method 2 described later immediately after preparation and after accelerated testing at 50° C. for 1 month.

An example of chromatograms of samples 34–36 prepared with methionine in various amounts shown in Table 2 (containing a fixed amount of phenylalanine and arginine and 0 mg, 0.1 mg or 1 mg methionine) as assayed by method 2 after accelerated testing at 60° C. for 2 weeks is shown in FIG. 1 and an example of chromatograms of said samples as assayed by method 2 immediately after preparation and after accelerated testing at 50° C. for 1 month is shown in FIG. 2.

Content Met-oxidized G-CSF was observed both immediately after preparation and after storage at 50° C. for 1 month of the sample containing no methionine (sample 34), while content of Met-oxidized G-CSF could be completely inhibited even after long-term storage by adding 0.1 mg or more of methionine.

The results of the content of Met-oxidized G-CSF calculated by the equation shown in method 2 are shown in table 9.

TABLE 9

| | Sample 34<br>0 mg Met | Sample 35<br>0.1 mg Met | Sample 36<br>1 mg Met |
|---|---|---|---|
| 50° C., 1 month | 1.2% | N.D. | N.D. |
| 60° C., 2 weeks | 1.7% | N.D. | N.D. |

N.D.: below detection limit.

Thus, content of Met-oxidized G-CSF could be completely inhibited by adding 0.1 mg or more of methionine.

Example 6

Addition of Methionine to Parathyroid Hormone Solution Formulations has an Inhibitory Effect Against Oxidation of Methionine Residues Formulated solutions of samples 37–39 containing 200 μg/mL of parathyroid hormone having 1–84 residues (hereinafter abbreviated as PTH) (prepared by the process described in WO9014415) and other components in the amounts shown in Table 10 below were prepared and aseptic-filtered, and then precisely 1 mL each was aseptically packed in a vial, which was completely capped to prepare PTH solution formulations.

TABLE 10

| | PTH | Methionine | Polysorbate 20 | pH (Citrate/phosphate buffer) |
|---|---|---|---|---|
| Sample 37 | 200 μg/mL | No | 0.01% | 6.5 |
| Sample 38 | 200 μg/mL | 0.01% | 0.01% | 6.5 |
| Sample 39 | 200 μg/mL | 0.1% | 0.01% | 6.5 |

Thus aseptically prepared PTH-containing solution formulations were allowed to stand in an incubator at 50° C. for 3 days.

The PTH content in each sample was assayed by reverse phase high-speed liquid chromatography using a C18 reverse phase column (4.6 mm×250 mm, 300 angstroms) with a mobile phase consisting of pure water, acetonitrile and trifluoroacetic acid. The amount equivalent to 10 μg of PTH was injected and PTH was eluted with an acetonitrile gradient and spectroscopically detected at a wavelength of 215 nm.

Figure 3:
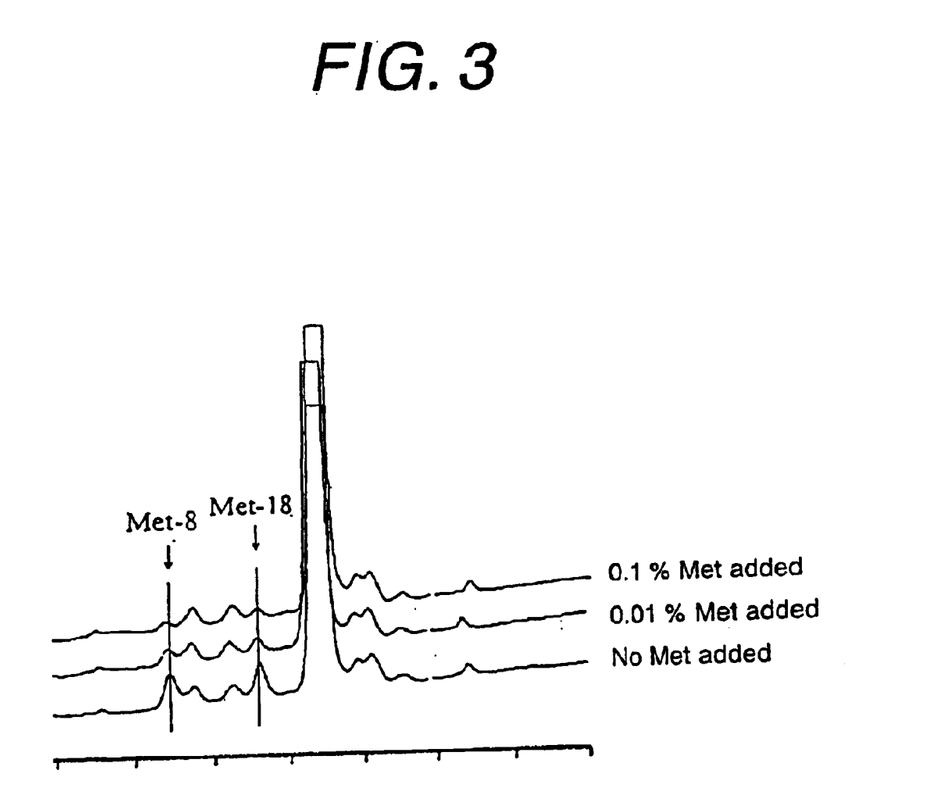
FIG. 3 shows HPLC chromatograms of parathyroid hormone solution formulations as assayed by the method shown in example 6 (storage at 50° C. for 3 days), which demonstrate that addition of methionine has an inhibitory effect against oxidation of methionine residues.

In this test series, PTH oxidized at the 8th methionine residue and PTH oxidized at the 18th methionine residue are detected immediately before intact PTH as shown in FIG. 3. The chromatograms show that oxidation at the 8th methionine residue in PTH and oxidation at the 18th methionine residue in PTH can be inhibited by adding methionine to formulations. They also show that addition of methionine into formulations has no influence on chemical decomposition reactions other than those of methionine residues. That is, addition of methionine into formulations can specifically improve only inhibition of oxidation of the protein at methionine residues without influencing other chemical decomposition reactions.

INDUSTRIAL APPLICABILITY

G-CSF formulations of the present invention are stable formulations that show a very high residual ratio of G-CSF even after long-term storage and that can almost completely inhibit oxidation of G-CSF at methionine residues.

What is claimed is:

1. A stable G-CSF formulation containing one or more amino acids selected from the group consisting of lysine, histidine, arginine, aspartic acid, glutamic acid, threonine and asparagine; one or more amino acids selected from hydrophobic amino acids; and methionine.

2. The G-CSF formulation of claim 1 having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks and a content of Met-oxidized G-CSF of 1% or less after accelerated testing at 50° C. for 1 month or after accelerated testing at 60° C. for 2 weeks.

3. The G-CSF formulation of claim 1 wherein said hydrophobic amino acid is selected from phenylalanine, tryptophan and leucine.

4. The G-CSF formulation of claim 1 containing one or more amino acids selected from the group consisting of lysine, histidine, arginine, aspartic acid and glutamic acid; one or more amino acids selected from the group consisting of phenylalanine, tryptophan and leucine; and methionine.

5. The G-CSF formulation of claim 1 containing phenylalanine, arginine and methionine.

6. The G-CSF formulation of claim 1, which is substantially free from protein as a stabilizer.

7. The G-CSF formulation of claim 1 in the form of a lyophilized formulation.

8. The G-CSF formulation of claim 1 further containing mannitol.

9. The G-CSF formulation of claim 1 further containing a surfactant.

10. The G-CSF formulation of claim 9 wherein said surfactant is a polyoxyethylene sorbitan alkyl ester.

11. The G-CSF formulation of claim 10 wherein said surfactant is Polysorbate 20 and/or 80.

12. The G-CSF formulation of claim 1, which has a pH of 5–7.

13. The G-CSF formulation of claim 12, which has a pH of 5.5–6.8.

14. The G-CSF formulation of claim 13, which has a pH of 6.5.

15. The G-CSF formulation of claim 1 wherein G-CSF is produced from CHO cells.

16. A stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month of a residual ratio of G-CSF of 90% or more after accelerated testing at 60° C. for 2 weeks, characterized in that it contains one or more amino acids selected from the group consisting of lysine, histidine, aspartic acid, glutamic acid, threonine and asparagine; and one or more amino acids selected from hydrophobic amino acids; and it has a pH of 5–7.

17. A stable G-CSF formulation according to claim 16, characterized in that it contains one or more amino acids selected from the group consisting of lysine, histidine, aspartic acid and glutamic acid; and one or more amino acids selected from the group consisting of phenylalanine, tryptophan and leucine; and it has a pH of 5–7.

18. A stable G-CSF formulation having a residual ratio of G-CSF of 90% or more after long-term storage testing at 25° C. for 3 months or a residual ratio of G-CSF of 90% or more after long-term storage testing at 40° C. for 2 months or a residual ratio of G-CSF of 90% or more after accelerated testing at 50° C. for 1 month or a residual ratio of G-CSF of 90% or more after accelerated testing at 60° C. for 2 weeks, characterized in that it contains one or more amino acids selected from the group consisting of lysine, histidine, arginine, aspartic acid, glutamic acid, threonine and asparagine; and one or more amino acids selected from the group consisting of tryptophan and leucine; and it has a pH of 5–7.

19. A stable G-CSF formulation according to claim 18, characterized in that it contains one or more amino acids selected from the group consisting of lysine, histidine, arginine, aspartic acid and glutamic acid; and one or more amino acids selected from the group consisting of tryptophan and leucine; and it has a pH of 5–7.

20. The G-CSF formulation of claim 16 or 18, which has a pH of 6.5.

* * * * *